(12) United States Patent
Ferrone (10) Patent No.: US 6,177,034 B1
(45) Date of Patent: Jan. 23, 2001

(54) METHODS FOR MAKING PROSTHETIC SURFACES

(75) Inventor: Thomas Ferrone, Roscoe, NY (US)

(73) Assignee: A-Pear Biometric Replications Inc., Roscoe, NY (US)

( * ) Notice: Under 35 U.S.C. 154(b), the term of this patent shall be extended for 0 days.

(21) Appl. No.: 09/054,713

(22) Filed: Apr. 3, 1998

(51) Int. Cl.[7] .............................. G01B 7/00; G06K 9/36

(52) U.S. Cl. .................. 264/40.1; 264/102; 264/129; 264/162; 264/219; 264/222; 264/223; 264/226; 264/227; 264/241; 264/245; 264/255; 264/267; 264/269; 264/279; 264/DIG. 30; 425/2; 345/425; 345/430; 382/285

(58) Field of Search .................. 264/40.1, 219, 264/129, 222, 223, 226, 227, 102, 245, 241, 255, 267, 268, 279, DIG. 30, 162; 425/2; 156/59; 345/425, 430; 382/285

(56) References Cited

U.S. PATENT DOCUMENTS

| 2,453,604 | 11/1948 | Tenenbaum et al. | 18/47.5 |
| 2,657,394 | 11/1953 | Milton, Jr. et al. | 3/12 |
| 2,810,161 | 10/1957 | Milton, Jr. et al. | 18/47.5 |

(List continued on next page.)

FOREIGN PATENT DOCUMENTS

| 28 01 299 A1 | 7/1979 | (DE) . |
| 2 333 486 | 7/1977 | (FR) . |
| 1342494 A1 | 10/1987 | (SU) . |

OTHER PUBLICATIONS

E.R. Bonnecarrere et al., "Case Report: Upper Extremity Soft–Tissue Reconstruction by Alloplastic Implant: Long–Term Result and Follow–up," *Annals of Plastic Surgery*, vol. 38, No. 1, pp. 74–76 (Jan., 1997).

G.S. Campbell et al., "Low Cost Cosmetic Hand Prostheses," *The Journal of Hand Surgery*, vol. 17B, No. 2, pp. 201–203 (Apr., 1992).

Monique M.C. Derhaag et al., "Personality Development in One–handed Children Treated with Myoelectrically Controlled Prosthesis," *The Journal of Rehabilitation*, vol. 56, No. 3, pp. 25–29 (Jul./Aug./Sep. 1990).

Gordon Kenworthy et al., "New techniques used in the production of cosmetic gloves, " *Medical and Biological Engineering*, pp. 120–123 (Jan., 1974).

Lewis A. Leavitt et al., "Cosmetic Cover for Endoskeletal Prosthetic Systems, a New Technique," *Archives of Physical Medicine and Rehabilitation*, vol. 56, pp. 414–416 (Sep., 1975).

D.A. O'Farrell et al., "Long–Term Follow–Up of 50 Duke Silicone Prosthetic Fingers," *The Journal of Hand Surgery*, vol 21B, No. 5, pp. 696–700 (Oct. 1996).

Barry Taylor et al., "Clinical Evaluation of the Franklin Applied Physics Cosmetic Cover for Lower Limb Prostheses: A Preliminary Report," *Journal of Rehabilitation Research and Devolopment*, vol. 32, No.1, pp. 74–78 (Feb., 1995).

(List continued on next page.)

*Primary Examiner*—Mathieu D. Vargot
*Assistant Examiner*—Suzanne E. McDowell
(74) *Attorney, Agent, or Firm*—Fish & Neave (57) ABSTRACT

Methods for reproducing a 3D object surface are provided. A preferred method according to this invention includes (1) identifying a real object surface, (2) acquiring at least a 3D data set with a 3D surface imaging device, (3) acquiring at least a 2D data set using a 2D surface imaging device with a surface resolution of at least about 0.1 mm$^2$, (4) synthesizing a 3D composite data set by orienting a first virtual image of the first data set and a second virtual image of the second data set to form a composite virtual image that corresponds to the composite data set, and (5) making a reproduction of the object surface with the composite data set. Orientation of the virtual images is relative to each other and without substantial loss of surface resolution.

46 Claims, 5 Drawing Sheets

U.S. PATENT DOCUMENTS

| | | | |
|---|---|---|---|
| 3,914,031 | 10/1975 | Sisler | 350/298 |
| 4,007,496 | 2/1977 | Glabiszewski | 3/2 |
| 4,258,441 | 3/1981 | Bell | 3/12.6 |
| 4,291,421 | 9/1981 | Massey et al. | 3/12.6 |
| 4,385,360 | 5/1983 | Yamada et al. | 363/514 |
| 4,436,684 | 3/1984 | White | 264/138 |
| 4,445,234 | 5/1984 | Ogunro | 3/1 |
| 4,558,420 | 12/1985 | Gerber | 364/476 |
| 4,559,055 | 12/1985 | Ogunro | 623/11 |
| 4,611,288 | 9/1986 | Duret et al. | 364/474 |
| 4,676,802 | 6/1987 | Tofield et al. | 523/66 |
| 4,685,924 | 8/1987 | Massey | 623/63 |
| 4,735,754 | 4/1988 | Buckner | 264/40.1 |
| 4,753,656 | 6/1988 | Tofield et al. | 623/15 |
| 4,792,338 | 12/1988 | Rennerfelt | 623/64 |
| 4,865,613 | 9/1989 | Rizzo | 623/65 |
| 4,990,162 | 2/1991 | LeBlanc et al. | 623/63 |
| 5,013,326 | 5/1991 | Horvath | 623/64 |
| 5,056,204 | 10/1991 | Bartschi | 29/169.5 |
| 5,060,678 | 10/1991 | Bauman et al. | 132/73 |
| 5,070,892 | 12/1991 | Trematerra | 132/73 |
| 5,080,681 | 1/1992 | Erb | 623/63 |
| 5,095,849 | 3/1992 | Cutler | 118/326 |
| 5,156,777 | 10/1992 | Kaye | 254/40.1 |
| 5,219,364 | 6/1993 | Lloyd | 623/33 |
| 5,222,986 | 6/1993 | Wright | 623/64 |
| 5,336,270 | 8/1994 | Lloyd | 623/33 |
| 5,376,323 | 12/1994 | Eaton | 264/222 |
| 5,378,033 | 1/1995 | Guo et al. | 294/116 |
| 5,432,703 | 7/1995 | Clynch et al. | 364/474.05 |
| 5,452,219 | 9/1995 | Dehoff et al. | 365/474.05 |
| 5,452,407 | 9/1995 | Crook | 395/121 |
| 5,487,012 | 1/1996 | Topholm et al. | 364/474.05 |
| 5,510,995 | 4/1996 | Oliver | 364/474.24 |
| 5,539,649 | 7/1996 | Walsh | 364/474.05 |
| 5,543,103 | 8/1996 | Hogan et al. | 264/219 |
| 5,596,503 | 1/1997 | Flint | 364/468.25 |
| 5,658,415 | 8/1997 | Montemurro et al. | 156/331.2 |
| 5,841,441 * | 11/1998 | Smith | 345/430 |
| 5,880,964 * | 3/1999 | Schall et al. | 364/474.01 |

OTHER PUBLICATIONS

"Is it real or is it digitized?," *Machine Design*, pp. 12 and 13 (April 9, 1992).

"Livingskin™ prostheses,"Aesthetic Concerns Prosthetics, Inc. (1997).

"The $28 Foot," *Time*, pp. 54 and 55 (Fall, 1997).

* cited by examiner

METHODS FOR MAKING PROSTHETIC SURFACES

BACKGROUND OF THE INVENTION

This invention relates to methods for reproducing a three-dimensional surface, and more particularly to methods for making surfaces for use with prosthetic devices, such as gloves resembling hands, feet, fingers, and other similar articles.

One of the original techniques for making a prosthetic surface included making a plaster cast of a human limb that could be used to manufacture an artificial one. This method of manufacture had many drawbacks, including the appearance of a line in the artificial limb corresponding to the junction between the two halves of the mold. Moreover, the ridges and depressions that normally make up the surface of the limb, such as the ones that form fingerprints, were substantially eliminated in the manufacturing process because the plaster cast was not capable of capturing all of the detail that makes up the surface.

In order to improve the appearance of the artificial limb, cosmetic gloves and the like were developed that more closely approximate the natural appearance of human skin. See, e.g., Milton et al. U.S. Pat. No. 2,657,394. The manufacture of such gloves, however, still required a process of reversing a physical mold in order to properly match the artificial limb with a natural one. Mold reversal may involve cutting the mold into parts and reattaching them in a reversed orientation, forming seams and other undesirable surface effects that must be later eliminated, or at least diminished, in the final stages of making the glove. However, the elimination of such surface effects is imperfect and usually a slow, labor intensive process.

Moreover, a patient may desire one or more superficial differences between a left and right limb (such as the appearance of a birthmark or mole). These differences can be difficult to reliably incorporate in the reversed glove because they are usually sculpted into the glove mold. However, the quality of the sculpted mold strongly depends upon the skill and artistry of the sculptor, making this process unreliable at best.

Methods for making prosthetic devices with laser and ultrasonic digitizing systems are known. See, e.g., Clynch et al. U.S. Pat. No. 5,432,703 and Walsh et al. U.S. Pat. No. 5,539,649. However, these methods do not address the difficulty of reproducing high resolution prosthetic surfaces, let alone high resolution prosthetic surfaces for residual limbs. For example, Clynch et al. was mainly concerned with producing an accurately shaped socket for reception of a residual limb in a prosthetic structure. Furthermore, Walsh et al. was concerned with providing dimensional information with regard to the relative location of the limb, skin, and bone surfaces in three-dimensional space.

Thus, it would therefore be desirable to provide methods for accurately making high resolution surfaces, especially surfaces of prosthetic devices.

It would be particularly desirable to provide methods for reliably making a prosthetic skin that matches the skin of a real counterpart limb, including any cosmetic differences or details desired by a patient.

It would also be particularly desirable to provide methods for rapidly designing and making high-resolution prosthetic surfaces, without manufacturing multiple iterations.

SUMMARY OF THE INVENTION

It is therefore an object of this invention to provide methods for making high resolution surfaces, especially surfaces of prosthetic devices.

It is also an object of this invention to provide methods for reliably making a skin for covering a prosthetic device that precisely matches the skin of a counterpart limb, including any cosmetic differences or details desired by a patient.

It is yet another object of this invention to provide methods for rapidly designing high-resolution prosthetic surfaces in a flexible graphical environment and for making those prosthetic surfaces.

In accordance with one aspect of the present invention, a method for reproducing a three-dimensional (hereinafter, "3D") object surface is provided. The method includes (1) identifying a real object surface, (2) acquiring at least a 3D data set with a 3D surface imaging device, (3) acquiring at least a two-dimensional (hereinafter, "2D") data set using a second surface imaging device with a surface resolution of at least about 0.1 mm$^2$, (4) synthesizing a 3D composite data set by orienting a first virtual image of the first data set and a second virtual image of the second data set to form a composite virtual image that corresponds to the composite data set, and (5) making a reproduction of the object surface with the composite data set. Orientation of the virtual images is relative to each other and without substantial loss of surface resolution.

According to one particular aspect of this invention, a method for making a prosthetic skin for covering a prosthetic device is provided. The method includes (1) acquiring at least a first data set with a surface imaging device having a surface resolution of at least about 0.1 mm$^2$; (2) synthesizing a 3D composite data set from the first data set without substantial loss of the surface resolution; (3) providing the composite data set to a digitally controlled fabrication device; (4) fabricating a mold with the fabrication device using the composite data set, and (5) fabricating the prosthetic skin with the mold.

BRIEF DESCRIPTION OF THE DRAWINGS

The above and other objects and advantages of the invention will be apparent upon consideration of the following detailed description, taken in conjunction with the accompanying drawings, in which like reference characters refer to like parts throughout.

DETAILED DESCRIPTION OF THE DRAWINGS

Figure 1A:
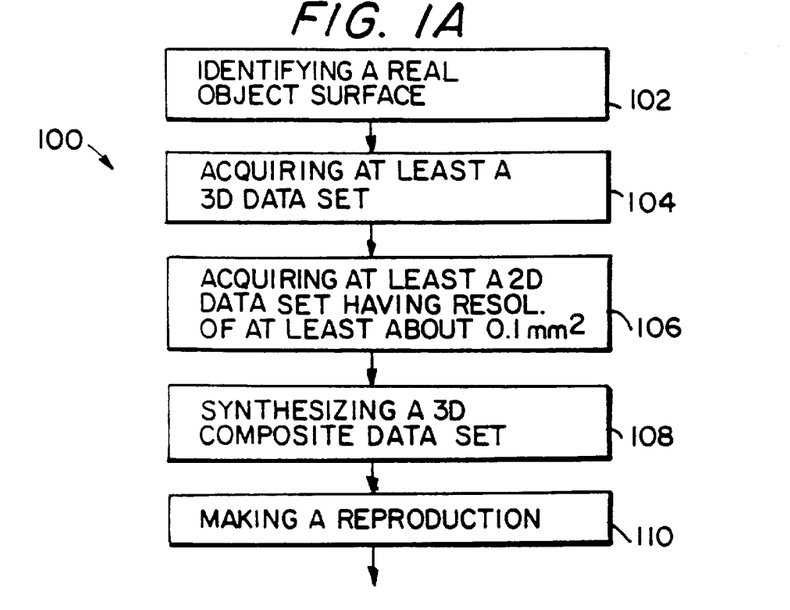
FIG. 1A is a flow chart of steps for carrying out one illustrative embodiment of a method according to this invention for making a reproduction of a three-dimensional surface of an object.

FIG. 1A is a flow chart of steps of method 100 according to this invention for reproducing a 3D object surface. Method 100 includes identifying a real object surface in step 102, acquiring at least a 3D data set with a 3D surface imaging device in step 104, acquiring at least a 2D data set using a second surface imaging device with a surface resolution of at least about 0.1 mm² in step 106, synthesizing a 3D composite data set by orienting a first virtual image of the first data set and a second virtual image of the second data set to form a composite virtual image that corresponds to the composite data set in step 108, and making a reproduction of the object surface with the composite data set in step 110. Orientation of the virtual images is relative to each other and without substantial loss of surface resolution.

In step 102, a real object is identified. A preferred real object for use with this invention is a human limb, in which case the surface of the object is the skin and nails that cover the limb. According to this invention, a limb may be an arm or a leg, or any part thereof. For example, if the object is a finger, the surface of the finger would include a relatively elastic skin portion and a relatively rigid finger nail portion. Similarly, if the object was a full hand, the surface would include, in addition to the elastic skin that covers most of the hand, four rigid finger nails and a rigid thumb nail. Because the texture and hardness of skin and nails are so different, it is often desirable to make these components separately. Also, these differences may mandate that the nail and skin portions be characterized with different surface imaging devices. Moreover, when the invention is being used to make a prosthetic device, step 102 preferably includes interviewing the patient to ascertain any financial constraints, determining the level of surface resolution desired in the final prosthetic device or surface, and establishing cosmetic details that the patient may wish to have included on the surface prosthetic device.

In step 104, at least a 3D data set is acquired. The 3D data set depicts the 3D shape of the surface and is acquired with a 3D imaging device. Some of the 3D imaging devices that can be used according to this invention are sold by Cyberware, Inc., of Monterey, Calif. (available under model no. 3030), Digibotics, Inc., of Austin, Tex. (available under the trademark Digibot II®), Laser Design, Inc., of Minneapolis, Minn. (available under the trademark Surveyor® 3D Laser Digitizing System), and Real 3D, of Orlando, Fla. (available under the trademark RealScan 3D™). These 3D imaging devices are laser-based measuring devices and stereoscopic measuring devices, but other devices based on different technology (such as polarization and acoustic technologies) may also be used in accordance with this invention.

In step 106, a 2D data set is acquired having a surface resolution of at least about 0.1 mm². As used herein, surface resolution is the surface area of a single pixel, which is a discrete element that, when combined with other pixels, form an image. Thus, a surface resolution of 0.1 mm² can be formed by a square pixel having sides of (0.1) mm$^{1/2}$ each. Alternatively, a surface resolution of 0.1 mm² can be formed by a rectangular pixel having sides of 0.25 mm and 0.4 mm. Preferably, the surface resolution of the image is better than 0.1 mm², that is the area of each pixel of the image is smaller than 0.1 mm². A surface resolution of 0.05 mm² is preferred.

Acquiring the 2D data set in step 106 may involve photographing the object with a digital camera so that the data set at least has gray scale information (e.g., a digital black and white photograph). The 2D data set may also contain color information (e.g., a digitized color photograph). Alternatively, the 2D data set acquired in step 106 is a two step process: (1) photographing the object with an analog camera to create an analog photograph and (2) digitizing the analog photograph to create a 2D data set representing the analog photograph. Again, the 2D data set should at least include gray scale information, but may include color information.

In addition to photographing the object, the 2D data set may be acquired in other ways. A first way includes making a drawing by an artist and digitizing that drawing with an imaging device to obtain an accurate 2D data set that represents the drawing. A second way includes making a projected outline by tracing the object and digitizing the outline to obtain a 2D data set that represents that outline. The difference between an outline and a drawing is that an outline merely describes the boundary or shape of the object, while a drawing contains more, such as surface detail.

Yet another way to acquire a 2D data set in accordance with this invention involves measuring the object with a tape measure to obtain at least one measurable dimension, such as a length or a circumference of the object. The tape is useful to confirm that at least one actual physical dimension of the composite virtual image is accurate.

Acquiring data sets in steps 104 and 106 can be direct or indirect. Direct data acquisition involves accumulating a data set directly from a real surface, such as a hand. Indirect data acquisition involves at least three steps: (1) building a negative mold of the object surface using a room temperature vulcanization technique; (2) building a positive model of the object surface using the negative mold; and (3) accumulating a data set depicting the positive model surface. If accumulating the data set depends on the reflectivity of the object surface (i.e., the real surface or the positive mold surface), a method according to a further aspect of this invention includes depositing a highly reflective coating on that surface before accumulating the 2D or 3D data sets. A highly reflective coating according to this invention may include zinc or titanium oxide.

The negative mold may be built by impressing an object (e.g., a hand) in a high-resolution moldable material that substantially preserves the surface details of the object. One example of a high-resolution material is a room temperature vulcanization ("RTV") molding material, such as a silicone material available under model No. 3110, sold by the Dow Corning Corporation, of Midland, Mich. As an alternative to using an RTV molding material, an alginate may be used.

Moreover, each of steps 104 and 106 can involve acquiring two or more data sets each. That is, step 104 may involve acquiring two or more 3D data sets and combining them in step 108 to form a composite 3D data set. Similarly, multiple 2D data sets can be used to characterize the surface of the object. For example, if the object being reproduced is a hand, a separate 2D data set can be used to characterize each finger nail, finger print, knuckle, and palm print (see, e.g., FIG. 2). One reason for acquiring multiple data sets is to ensure that a proper level of detail is obtained for the entire 3D surface being reproduced. The number of 2D and 3D data sets acquired in steps 104 and 106 depends on the resolution of the surface imaging devices available and any financial constraints determined in step 102.

In step 108, a 3D composite data set is synthesized by orienting a first virtual image of the first data set and a second virtual image of the second data set to form a composite virtual image. The orientation of the first and second virtual images is performed relative to each other and is accomplished without a substantial loss of surface resolution. Synthesis of the composite data set may be performed with conventional 3D data editing software (such as the ones sold by NewTek, of San Antonio, Tex. (available under the trademark LightWave 3D®), Cyberware, Inc., of Monterey, Calif. (available under the trademarks CyDir Digitizing Environment&, CyClice IGES Slicing Software®, CySurf Surfacing Software®, and CySculpt Sculpting Software®).

Synthesis of the composite data set in step 108 is performed by orienting first and second virtual images. The first and second virtual images correspond to the 2D and 3D data sets, respectively, and are used to create a composite virtual image. Synthesis preferably take place in a highly interactive and flexible environment so that the composite image, and corresponding composite data set, can be edited in stages from multiple perspectives until a final composite data set is created. Synthesis at least includes combining two data sets to form a composite data set, preferably by seamlessly draping a 2D data over a 3D data set. This process is sometimes referred to as "bump mapping." Synthesis may further include reversing one or more data sets and creating data subsets.

Figure 2:
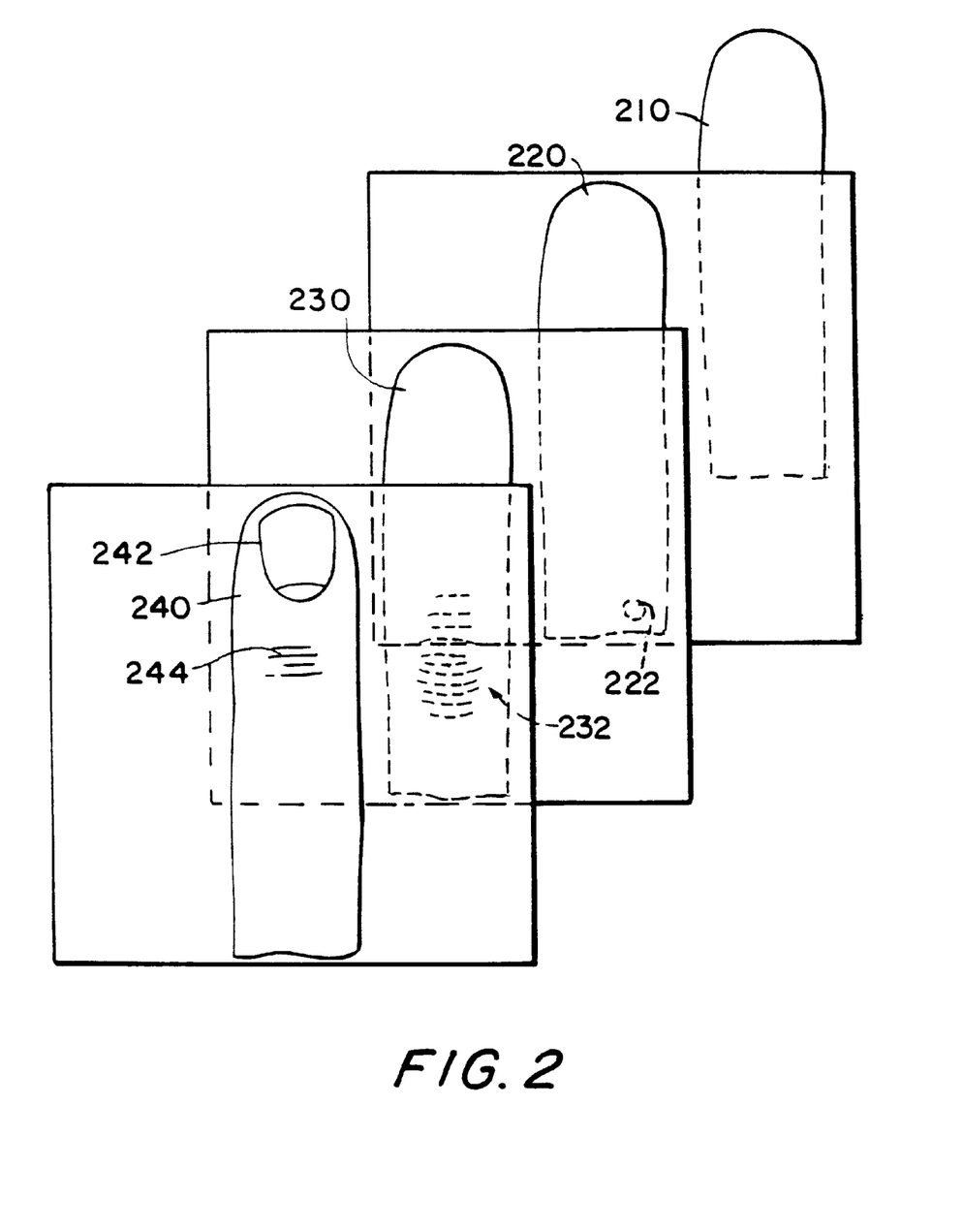
FIG. 2 shows four simplified data sets that are being oriented with respect to each other to synthesize a composite data set according to this invention.

FIG. 2 shows four data sets that may be used to synthesize a composite data set according to step 108 of this invention. First virtual image 210 corresponds to a first 3D data set that depicts the general 3D shape of a finger. In addition to depicting the general shape of the finger, image 210 may contain substantial texture and color information. Second virtual image 220 corresponds to a 2D data set that includes one cosmetic detail: birthmark 222. Of course, image 220 may also include other cosmetic details, including an erasure of an undesirable surface feature. Third virtual image 230 corresponds to a 2D data set that includes surface texture 232 over the length of the finger. The surface texture can be obtained from a black and white photograph as described above. Fourth virtual image 240 corresponds to a 2D data set that includes additional surface features near the tip of the finger, including finger nail 242 and skin folds 244. The surface features contained in virtual image 240 may also be obtained from a photograph of the finger.

Figure 3:
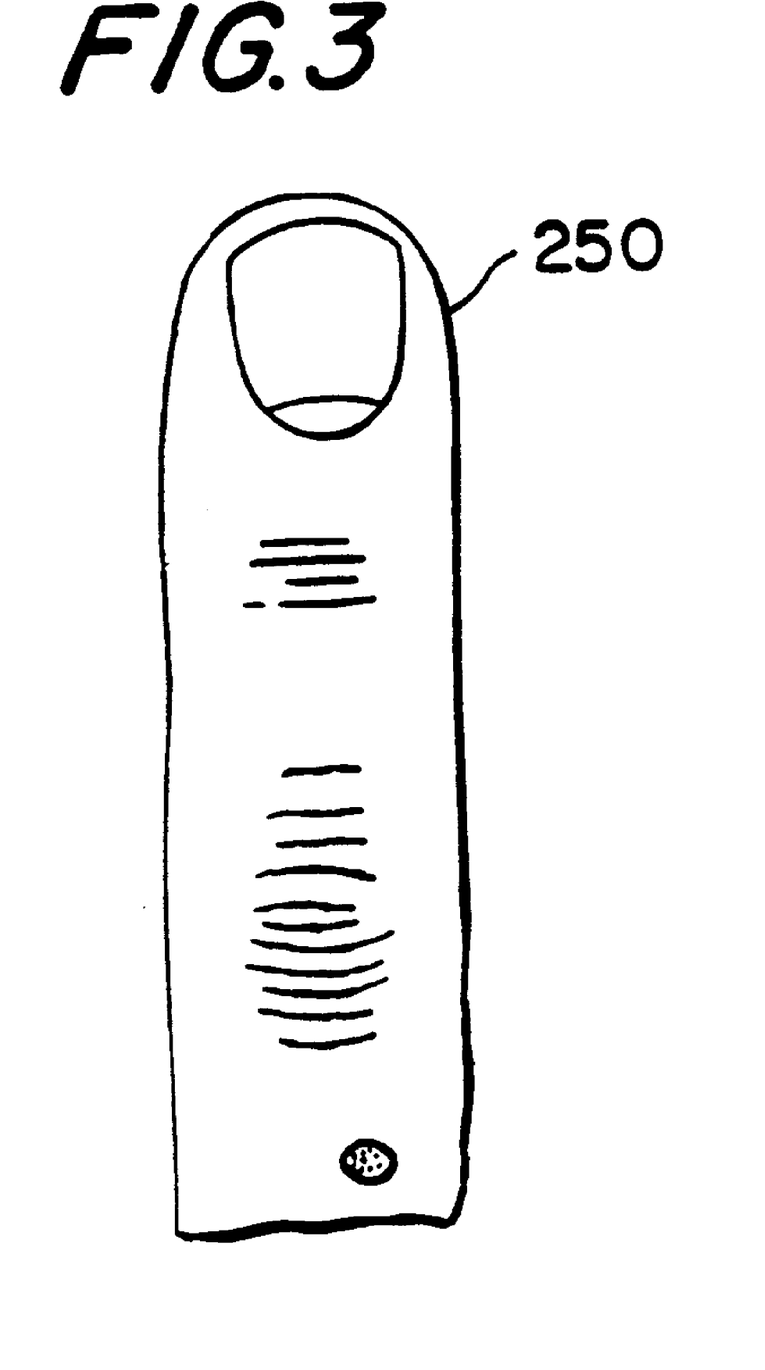
FIG. 3 shows a simplified virtual image that corresponds to the composite data set synthesized using the four data sets shown in FIG. 2 according to this invention.

FIG. 3 shows a composite virtual image 250 that contains substantially all of the information shown in virtual images 210, 220, 230, and 240. Additional data sets may be needed to define or enhance a finger print on the other side of the finger. In a preferred embodiment, orientation of the virtual images is performed while viewing them on a visual display device, including a virtual reality device. Also, it should be clear to one of ordinary skill in the art that the process of synthesizing a composite data set by overlaying multiple data sets, as shown by FIGS. 2 and 3, can be performed iteratively until a satisfactory composite image, and thereby composite data set, is synthesized. This may involve acquiring additional data sets at any time during the process according to this invention and incorporating them into a first or subsequent iteration of a synthesized composite data set. The ability to quickly create multiple iterations of virtual images before manufacturing means that development costs are reduced and reproduction quality is improved.

Although the virtual image may be an accurate representation of the real object being measured, that virtual image may be modified, or enhanced, with one or more cosmetic details desired by modifying a target data set. A target data set may be any of the data sets used in accordance with this invention, including the 3D data set, the 2D data set, and the composite data set and/or subset. A cosmetic detail may be a kinetic detail, an authentic detail, or a desired detail.

A kinetic detail is a surface feature that results when the real object moves, but does not appear in any of the 3D or 2D data sets. An example of a kinetic detail is a skin fold at a wrist that only appears when the wrist is in a bent position.

An authentic detail is a surface feature that actually appeared on the object being replaced but is no longer available for imaging. For example, if a patient was missing a right arm that had a birthmark, a reproduction can be made according to this invention by acquiring data depicting the left arm without a birthmark, synthesizing a composite data set by reversing the left arm data and adding a birthmark to it, and making a right arm prosthetic device that includes the birthmark. Thus, the prosthetic device would be substantially the same as the left arm, but would include a birthmark. Alternatively, a blemish, such as a scar, may be removed from a data set by replacing the data that define the blemish with new data that do not contain the blemish. Thus, birthmarks and scars are examples of authentic details according to this invention.

Finally, a desired detail is a surface feature that has no real basis, but is nonetheless desired. For example, desired details may be birthmarks, tattoos, hair, and freckles.

As discussed above, synthesis of a composite data set in step 108 may include reversing a data set, which involves calculating a new data set that depicts a mirror image of an original data set. Most conventional 3D imaging software can do this, including most of the 3D imaging software packages listed above. For purposes of this invention, it makes no difference whether reversal occurs before or after a composite data set is created. For example, if the real object being copied is a right thumb, the 3D data set would depict the general shape of the thumb and the 2D data set would depict the thumb texture, color and other surface features, such as a thumb print. Thus, the composite data set can be synthesized by combining the 2D and 3D data sets before reversing them, or by reversing the 2D and 3D data sets before combining them. In either case, the composite data set that results can be used to make a reversed reproduction of the real object surface.

The use of a reversed data set for making a prosthetic device is an important aspect of this invention. Conventional techniques for making a prosthetic device require physical reversal of a mold of a counterpart limb. However, mold reversal may involve cutting the mold into parts and reattaching them in a reversed orientation, forming seams and other undesirable surface effects that must be dealt with after a prototype of the prosthetic device is made. Mold reversal is usually slow, labor intensive, and costly. By reversing a data set before making a mold, these disadvantages are largely eliminated.

According to this invention, a composite data subset may also be synthesized in step 108. As used herein, a composite data subset is any data set depicting any portion of the surface of a composite virtual image. A subset may be synthesized by selecting a portion of the surface of a virtual composite image and then creating the composite data subset, such as by storing the data that correspond to that portion. Alternatively, a subset may be created directly from a 2D or a 3D data set acquired from a patient or generated from a collection of prototypes. The composite data subset is preferably separately manipulatable from the composite data set. An example of a composite data subset is one that depicts a finger nail.

Multiple composite data subsets may be used in accordance with this invention. For example, a left hand prosthesis may have seven separately defined surfaces that correspond to seven composite data subsets. In this example, a first surface may correspond to a reversed image of a patient's right hand, a second surface may correspond to the patient's left wrist stump against which the prosthesis will fit, and five additional surfaces may correspond to one thumb nail and four finger nails. Because composite data subsets are separate entities, each corresponding surface can be made separately with different materials if desired.

Preferably, the composite data set and/or subset is calibrated by comparing a measurable dimension of the real object with the same dimension of the composite set or subset. For example, if the object is a human finger, a measurable dimension might be a circumference of the finger at a knuckle. The circumference of the finger at the knuckle can be measured directly with a tape measure. That measured circumference may be used to calibrate the circumference of the respective knuckle of a composite virtual image. If a circumference of the composite virtual image is too large or small, the composite data set can be reduced or enlarged, respectively, so that the virtual image is properly calibrated and accurately represents the real or reversed object.

Synthesis of the composite data set in step 108 may further include increasing a contrast level of a data set. The contrast level of a data set represents the degree of difference between the light and dark pixels of an image. So, if every pixel of a 2D image is assigned a value between 1 and 255, an image with relatively few pixels in the middle of that range would have a higher contrast level than an image with a relatively large number of pixels in the middle of that range. By increasing the contrast level, the amount of noise in the data set can be reduced, which improves the bump mapping process and the quality of the reproduction made therefrom. Therefore, the contrast level of the first data set, second data set, and/or the composite data set or subset can be increased by deleting a middle portion of a gray scale associated with the data.

The contrast level of the composite data set is preferably made substantially uniform over the surface of the composite image. For example, if the 3D data set has a low noise level and the 2D data set has a relatively high noise level, the contrast level of one or both of these data sets may be modified before being synthesized into a composite data set. Alternatively, the contrast level of any portion of the composite data set may be modified as desired.

After the contrast level of the composite data set is made substantially uniform, mold information is added to the composite data set. Mold information specifies the structure and thickness of the mold used to fabricate a reproduction according to this invention. Preferably, adding mold information includes orienting a matrix of virtual structural elements relative to the virtual composite image. Because mold material is generally expensive, it is desirable that the mold be thin to conserve material, but thick enough to support the lining of the mold and the reproduction during fabrication.

Figure 4A:
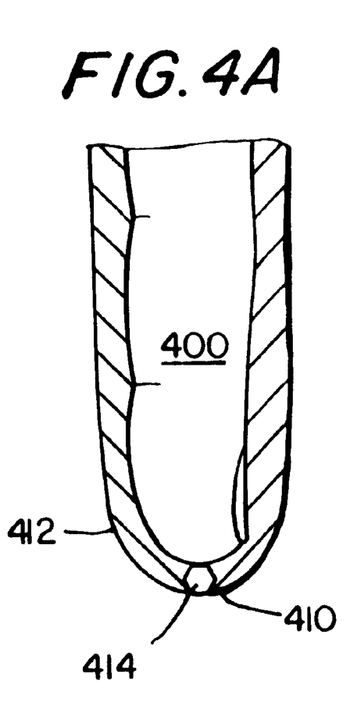
FIGS. 4A–4C show simplified longitudinal cross-sectional views of three images of molds having different thicknesses for use in making a prosthetic skin of a finger according to this invention. The thicknesses of the images of the molds are exaggerated relative to the size of the finger to make certain features of the mold more visible.
Figure 4B:
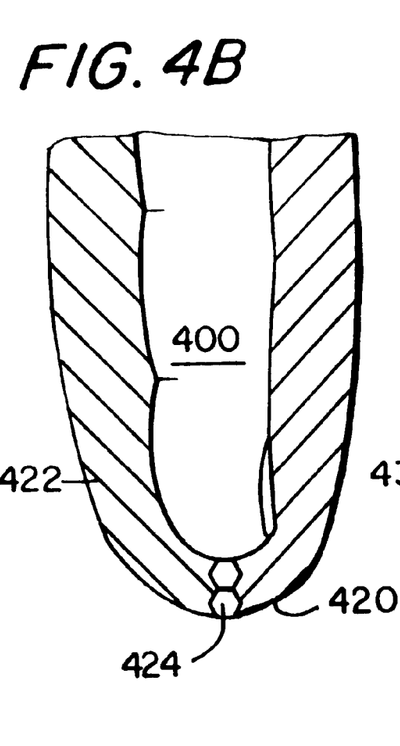
Figure 4C:
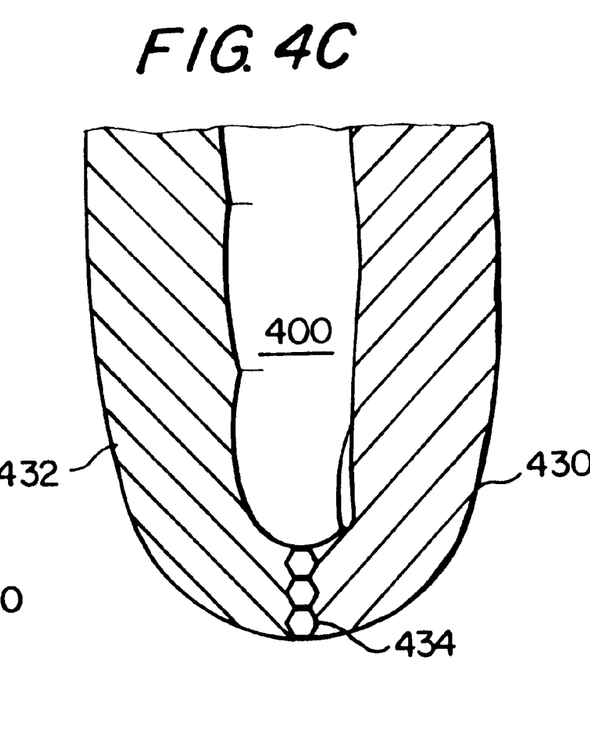

For example, FIGS. 4A–4C show cross-sectional areas of three virtual composite images 410, 420, and 430, respectively, of finger mold cavity 400. The thicknesses of the mold images are exaggerated relative to the size of the finger to make certain features of the mold more visible. FIG. 4A shows finger mold cavity 400 surrounded by a relatively thin layer of structural elements 412. FIGS. 4B and 4C show finger mold cavity 400 surrounded by successively thicker layers of structural elements 422 and 432, respectively. For purposes of making a prosthetic skin, the mold thickness is preferably between about 1.0 mm and about 10.0 mm, and most preferably about 2.0 mm.

Structural elements 412, 422, and 433 shown in FIGS. 4A–4C are substantially hollow to further conserve mold material. The structural elements are preferably tubular and have a polygonal cross-sectional area (e.g., hexagonal), to form a honeycomb-like structure. However, the cross-sectional areas of the structural elements may be any shape, including elliptical, if desired. The desired orientation of the tubular structures that make up the mold depends on the viscosity of the material used to invest the mold. The molds shown in FIGS. 4A–4C have tubular elements with open ends oriented upward to prevent a low viscosity investing material from leaking out before it hardens. On the other hand, if the investing material is highly viscous, it would not leak and the upward orientation of the tubular elements would be unnecessary. Hexagonally shaped cross-sections 414, 424, and 434 of structural elements 412, 422, and 432 are shown at the bottom of FIGS. 4A–4C, respectively.

In addition to adding mold information, synthesizing in step 108 preferably includes amending the composite data set so that a portion of the composite virtual image surface virtually conforms to a different virtual surface. For example, when the reproduction is a prosthetic device or skin, an amendment of the composite data set might be necessary to ensure that the device or skin comfortably conforms to a stump of a missing limb. Because the composite data set can be accurately amended according to this invention before a prosthetic device is made, the device has a higher likelihood of fitting the patient, without multiple iterations. Because the iterative process is the most expensive and time consuming part of a conventional manufacturing process, amendment of the composite data set before fabrication is very desirable.

In step 110, the final step of method 100, a reproduction is actually manufactured. Any available method can be used according to this invention, including using any of the mold-based fabrication techniques discussed below and other techniques that are not mold-based, such as a high-resolution milling techniques.

Figure 1B:
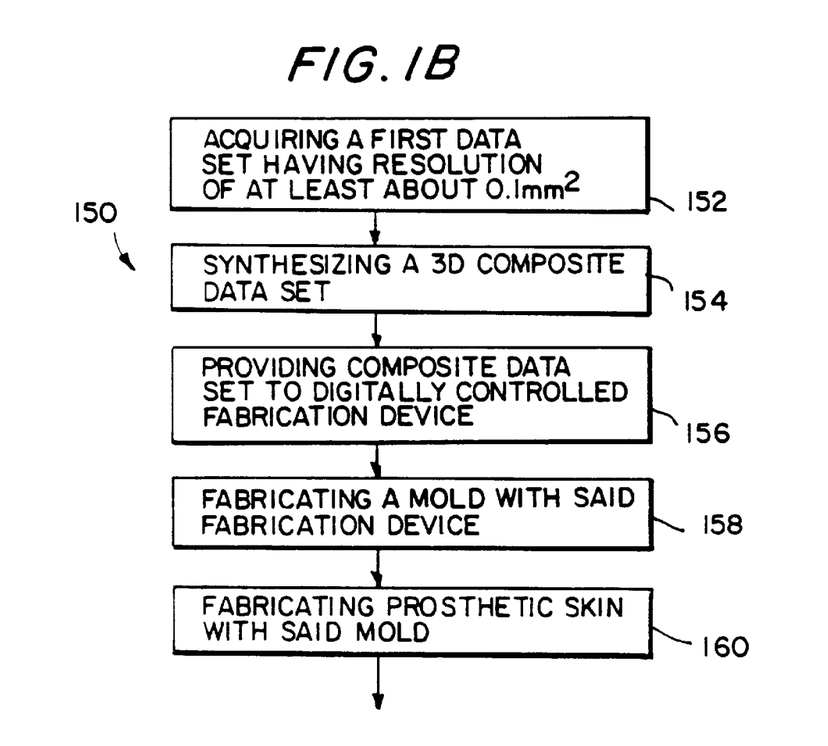
FIG. 1B is a flow chart of steps for carrying out another illustrative embodiment of a method according to this invention for making a prosthetic skin for covering a prosthetic device.

FIG. 1B is a flow chart of steps of method 150 according to another aspect of the present invention for making a prosthetic skin. The method includes acquiring at least a first data set with a surface imaging device having a surface resolution of at least about 0.1 mm$^2$ in step 152; synthesizing a 3D composite data set from the first data set without substantial loss of the surface resolution in step 154; providing the composite data set to a digitally controlled fabrication device in step 156; fabricating a mold with a fabrication device using the composite data set in step 158, and fabricating the prosthetic skin with the mold in step 160.

In step 152, at least a first data set is acquired with a surface imaging device. The first data set depicts the surface of an original limb and has a surface resolution of at least about 0.1 mm$^2$. As described above, any surface imaging device with sufficient surface resolution may be used to acquire the first data set, including 2D and 3D surface imaging devices.

The original limb may be the missing body part being replaced, such as when a patient is preparing for an impending amputation. Alternatively, the original limb may be a counterpart of the missing limb, in which case this method would include reversing the data set so that the prosthetic skin will correspond to the missing limb. For example, if the prosthetic device corresponds to a right index finger, the counterpart would be the left index finger and the prosthetic skin would be the outer layer of the prosthetic device. In another embodiment of the present invention, the original limb may not even be the patient's, such as when a patient is missing both arms. In that case, the first data set can be acquired from an arm of another person of desirable size and shape.

In step 154, a 3D composite data set is synthesized from the first data set. As described above, synthesis may result in a composite data set that is reversed relative to the first data set. As also already described above, the 3D composite data set may be synthesized by bump mapping, or embossing, a 3D data set with a high resolution 2D data set, or by any other technique that combines two or more data sets. Synthesis may also include processing a 3D composite data set by adding one or more cosmetic details to the first data set. However, regardless of how the 3D composite data set is synthesized, the surface resolution of the first data set according to this aspect of the invention, must be substantially maintained in the composite data set. Synthesis of a 3D composite data set in step 154 should also include adding mold information as described above.

After a 3D composite data set is synthesized in step 154, the composite data set is provided to a digitally controlled fabrication device in step 156. A digitally controlled fabrication device is any fabrication apparatus that can accept as input a data set that depicts the prosthetic skin and can make a mold of the skin. Examples of digitally controlled fabrication devices that can be used according to this invention include, but are not limited to, fused deposition modeling devices, stereo lithographic devices, 3D electroforming systems, laminated object manufacturing systems, solid ground curing devices, and 3D printing devices.

Figure 5:
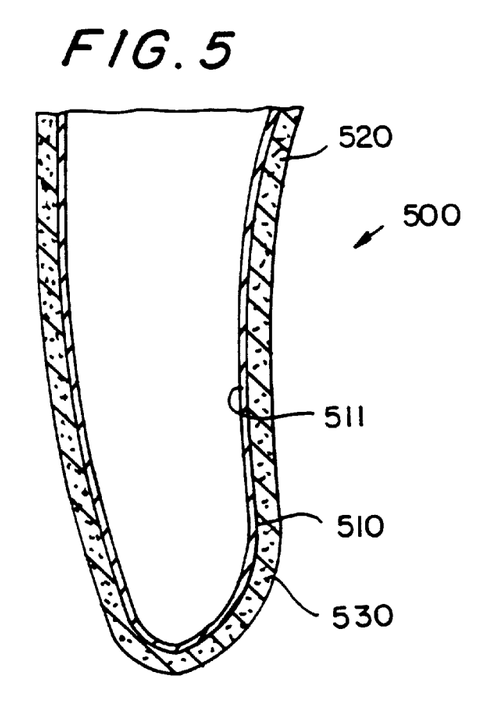
FIG. 5 shows a simplified longitudinal cross-sectional view of an illustrative mold fabricated according to this invention.

After providing a composite data set to the fabrication device in step 156, a negative mold is fabricated in step 158. FIG. 5 shows a longitudinal cross-section of a preferred embodiment of a mold fabricated according to this invention. Mold 500 preferably includes three components: lining 510, matrix of structural elements 520, and investing material 530. Inner surface 511 of lining 510 is the portion of mold 500 that contains the high resolution information of the composite data set that is used to make a prosthetic skin. Lining 510 may be any high resolution molding material, such as epoxy. One type of epoxy that may be used in accordance with this invention is available under model No. SL5195, sold by the Ciba Speciality Chemicals Corporation, of Los Angeles, Calif. The material used to make the mold, including the lining, must be capable of withstanding the temperatures used to cure the prosthetic material.

Figure 6:
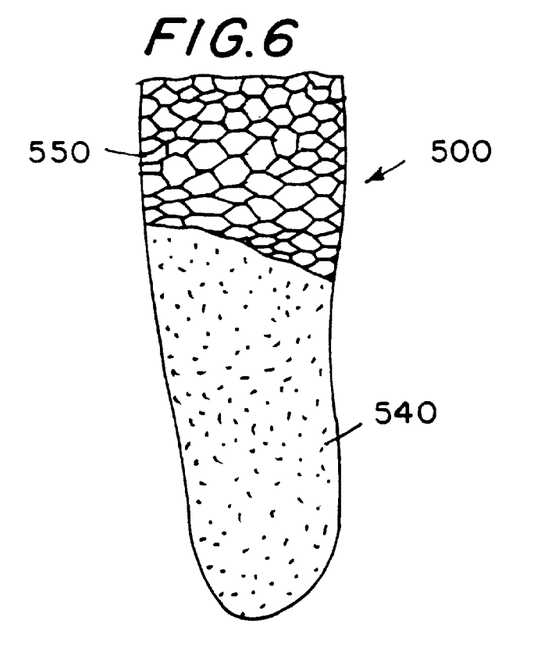
FIG. 6 shows a simplified longitudinal view, partly in section, of the illustrative mold shown in FIG. 5 before full investment according to this invention.

As discussed above, matrix 520 preferably includes multiple tubular elements that can be invested, or filled, with investing material 530. FIG. 6 shows a planar view of mold 500 before it is fully invested. Upper portion 550 of mold 500 shows the honeycomb structure formed by matrix 520 before being filled with investing material. Lower portion 540 of mold 500 shows the outer surface of the mold after the honeycomb structure is filled with investing material.

The negative mold fabricated in step 158 may be fabricated directly or indirectly. Indirect fabrication involves fabricating a positive mold, such as with a polymer wax material, and then fabricating a negative mold from the positive mold. One device capable of fabricating a positive mold with a polymer wax material is available under the trademark Acturn 2100® Modeler, sold by 3D Designs, of Valencia, Calif. Preferably, the material used to fabricate the negative mold is an epoxy, a phenolic resin, silicone, or an electroformed metal.

As shown in FIGS. 4–6, direct fabrication of a negative mold can include building a matrix of hollow structural elements that substantially conform to the outer surface of the prosthetic device to be made and investing the matrix with a matrix investing material. Preferably, the matrix investing material is a metal-epoxy resin, but can be any liquid capable of hardening in the matrix and capable of withstanding the temperatures used to cure the skin in step 160.

After the mold is fabricated, a prosthetic skin may be fabricated by coating a lining of the mold with at least one coat of silicone material. The coat may be a single thick coat or any number of thinner coats that together form a coat of desired thickness. In any case, the coat will include a first surface that substantially contacts the lining of the mold and a second surface that does not substantially contact the lining. Silicone material (such as the one sold under model No. Med. 6410 by Nu-Sil Technology of Carpinteria, Calif., or any other silicone material having substantially similar physical properties) is a preferred prosthetic material, however, any other material capable of providing a high resolution reproduction of the lining surface may be used.

The coating process preferably includes at least four steps—depositing, degassing, drying, and curing the material. Depositing the material may include pouring or spraying the material in liquid form onto the lining of the mold. Degassing involves removing volatile gases, including organic solvents, that normally are emitted by the material during hardening. Degassing may be achieved by applying a vacuum to the material before or after the material is deposited on the lining of the mold. If degassing is performed before the mold is coated, the vacuum may be applied to the vessel containing the material. If degassing is performed after the mold is coated, a vacuum may be applied through a port of the mold. The strength of the vacuum is not critical, but preferably less then about 30 bars. After a prosthetic material (such as silicone) is used to coat the mold surface, it may be dried while the mold is rotated. Rotation of the mold causes the material to flow evenly across the surface of the mold so that the prosthetic skin can harden with a substantially uniform thickness. After the material is at least substantially dried, the material may be cured, such as by heating it to a temperature above room temperature. As already described above, the mold must be capable of withstanding the temperature used to cure the prosthetic material. Thus, if a mold is made of an epoxy, such as Ciba Speciality Chemicals Corporation's epoxy model No. SL5195, the preferred curing temperature is less than about 400° F., and most preferably less than about 375° F.

When the coat of silicone material includes two or more constituent coats, those constituent coats may have different compositions. For example, the silica concentration of one coat may be different from the concentration of another coat. So, if the skin includes two coats, the first coat, which contacts the mold lining, can have a first concentration of silica, and the second coat, which does not contact the mold lining, can have a second concentration of silica greater than the first coat. One reason that it may be desirable to increase the concentration of silica in the second coat is that a high concentration of silica may improve the bond between the skin and the material used to fill the prosthetic skin, especially when the fill material is silicone-based. Another method of improving that bond is to roughen the surface. Some of the possible ways that the surface may be roughened include abrading, etching, brushing, or sandblasting the surface.

After the skin is properly cured, the method according to one aspect of the invention includes removing the skin from the mold and finishing the skin by adding color to the inner surface of the skin, such as by painting it. The inner surface of the skin refers to the surface of the prosthetic skin that faces toward the inside of the prosthetic device. The step of adding color to the inner surface may include adding any naturally occurring feature (e.g., freckles) or artificial feature (e.g., a tattoo).

In addition to adding color, the method according to this invention may include inserting an armature (e.g., a structural element) into the skin and filling the skin with a fill material, such as silicone or urethane foam. In this way, a complete prosthetic device can be made.

Thus it is seen that a method for reproducing a 3D surface, such as a prosthetic skin, is provided. The method involves acquiring at least one data set having a surface resolution of at least about 0.1 mm$^2$, synthesizing a 3D composite data set by orienting an image that corresponds to the data set, and making an accurate reproduction with the composite data set. One skilled in the art will appreciate that the present invention can be practiced by other than the described embodiments, which are presented for purposes of illustration and not of limitation, and the present invention is limited only by the claims which follow.

I claim:

1. A method for reproducing a 3D object surface comprising:

identifying a real object surface having at least one measurable dimension;

acquiring at least a 3D data set using a 3D imaging device, said 3D data set depicting said object surface;

acquiring at least a 2D second data set using a second surface imaging device, the second data set depicting said object surface and having a surface resolution;

synthesizing a 3D composite data set by combining said 3D data set and said 2D second data set through orienting, relative to each other and without substantial loss of said surface resolution, a first virtual image of said first data set and a second virtual image of said second data set to form a composite virtual image, said composite virtual image corresponding to said composite data set; and making a physical reproduction of said object surface with said composite data set.

2. The method of claim 1 wherein said acquiring said 3D data set comprises:

building a negative mold of said object surface;

building a positive mold of said real object surface using said negative mold; and accumulating said 3D data set depicting said positive model surface.

3. The method of claim 2 further comprising depositing a highly reflective coat on said positive mold before said accumulating.

4. The method of claim 2 wherein said building said negative mold comprises impressing said object in a moldable material selected from a group consisting of an RTV molding material and an alginate.

5. The method of claim 1 wherein said acquiring said 3D data set comprises scanning said object surface with said 3D imaging device selected from a group consisting of a laser measuring device, a stereoscopic measuring device, a polarization measuring device, and an ultrasonic measuring device.

6. The method of claim 5 wherein said acquiring said 2D data set comprises accumulating said 2D data set by photographing said object with a digital camera, said 2D data set having at least gray scale information.

7. The method of claim 5 wherein said acquiring said 2D data set comprises:

photographing said object with an analog camera to create an analog photograph; and digitizing said analog photograph to create said 2D data set depicting said photograph, said 2D data set having at least gray scale information.

8. The method of claim 5 wherein said acquiring said 2D data set comprises:

making a drawing by an artist; and digitizing said drawing to obtain said 2D data set depicting said drawing, said 2D data set having at least gray scale information.

9. The method of claim 5 wherein said acquiring said 2D data set comprises:

tracing said real object to obtain a projected outline; and digitizing said outline to obtain said 2D data set depicting said outline.

10. The method of claim 5 wherein said acquiring said 2D data set comprises:

photographing said object to obtain a projected outline; and digitizing said outline to obtain said 2D data set depicting said outline.

11. The method of claim 5 further comprising measuring said object with a tape measure to obtain said at least one measurable dimension.

12. The method of claim 5 wherein said synthesizing comprises reversing at least one of said data sets so that said making said reproduction comprises making a reverse reproduction.

13. The method of claim 12 wherein said reversing comprises reversing said composite data set.

14. The method of claim 5 further comprising synthesizing a composite data subset that depicts a portion of said surface of said virtual image.

15. The method of claim 14 wherein said synthesizing said subset comprises:

selecting said portion of said surface of said virtual image; and creating said composite data subset, said subset being separately manipulatable from said composite data set.

16. The method of claim 5 wherein said synthesizing said composite data set comprises calibrating said composite data set with said at least one measurable dimension.

17. The method of claim 5 further comprising modifying a target data set to include at least one cosmetic detail, said target data set being selected from a group consisting of said composite data set and said composite data subset.

18. The method of claim 17 wherein said modifying comprises modifying said target data set with a cosmetic detail selected from a group consisting of a kinetic detail, an authentic detail, and a desired detail.

19. The method of claim 5 wherein said synthesizing comprises increasing a contrast level of a target data set by deleting a middle portion of a gray scale associated with said target data set, said target data set being selected from a group consisting of said at least said 3D data set, said at least said 2D data set, and said composite data set.

20. The method of claim 5 wherein said synthesizing comprises establishing a substantially uniform contrast level in said composite data set.

21. The method of claim 5 wherein said synthesizing comprises adding mold information to said composite data set for fabricating a mold for making said reproduction, said mold information including mold structure information and mold thickness information.

22. The method of claim 21 wherein said adding mold information comprises orienting a matrix of virtual structural elements relative to said virtual composite image.

23. The method of claim 22 wherein said synthesizing comprises amending said composite data set so that a portion of said virtual image surface is adapted to accurately conform to a different virtual surface.

24. The method of claim 23 wherein said real object surface includes at least a first real surface and a second real surface, said first real surface being a surface of a human limb and said second real surface being a surface of a counterpart stump.

25. The method of claim 1 wherein said synthesizing comprises combining said first and second data sets according to a mapping process.

26. The method of claim 25 wherein said mapping is bump mapping.

27. The method of claim 25 wherein said mapping is embossing.

28. The method of claim 25 wherein said mapping is bump mapping.

29. The method of claim 25 wherein said mapping is embossing.

30. A method for making a prosthetic skin for covering a prosthetic device that replaces a missing limb that attaches to a stump, said method comprising:
   acquiring at least a first data set with a surface imaging device, said first data set depicting a surface of an original limb and having a surface resolution;
   synthesizing a 3D composite data set by combining a second data set with said first data set through orienting, relative to each other, a first virtual image of said first data set and a second virtual image of said second data set, said composite data set depicting said prosthetic skin without substantial loss of said surface resolution;
   providing said composite data set to a digitally controlled fabrication device, wherein said fabrication device is selected from a group comprising a fused deposition modeling device, stereo lithographic device, 3D electroforming system, a laminated object manufacturing system, a solid ground curing device, and a 3D printing device;
   fabricating a negative mold with said fabrication device using said composite data set, said mold substantially depicting said prosthetic skin; and
   fabricating said prosthetic skin with said mold.

31. The method of claim 30 wherein said original limb is said missing limb.

32. The method of claim 30 wherein said original limb is a counterpart of said missing limb, said method further comprising reversing one of said data sets so that said prosthetic skin substantially corresponds to said missing limb.

33. The method of claim 30 wherein said fabricating said mold comprises fabricating a negative mold with a high resolution epoxy.

34. The method of claim 30 wherein said fabricating said mold comprises:
   fabricating a positive mold with a polymer-wax; and
   fabricating a negative mold from said positive mold using a material selected from a group consisting of an epoxy, a phenolic resin, silicone, and an electroformed metal.

35. The method of claim 30 wherein said fabricating said negative mold comprises:
   building a lining that has the negative shape of said prosthetic skin;
   building a matrix of hollow structural elements according to said composite data set; and
   investing said matrix with a matrix investing material.

36. The method of claim 35 wherein said lining has a thickness between about 2 mm and about 10 mm.

37. The method of claim 35 wherein said matrix has a thickness of between about 1 mm and about 10 mm.

38. The method of claim 35 wherein said investing comprises investing said matrix with a metal-epoxy resin.

39. The method of claim 35 wherein said fabricating said skin comprises coating said lining with at least one coat of silicone material, said at least one coat having a first surface that substantially contacts said lining and a second surface that does not substantially contact said lining.

40. The method of claim 39 wherein said coating comprises:
   coating said lining with at least a first coat of silicone material that contacts said lining; and
   coating said first coat with at least a second coat of silicone material that substantially does not contact said lining, said second coat having a silica concentration greater than said first coat.

41. The method of claim 39 wherein said coating comprises:
   depositing said coat on said lining;
   degassing said silicone material;
   drying said coat while rotating said mold to ensure that said prosthetic skin has a substantially uniform thickness; and
   curing said coat by heating it above room temperature.

42. The method of claim 39 further comprising roughening said second surface of said coat.

43. The method of claim 39 further comprising:
   removing said prosthetic skin from said mold; and
   finishing said skin by adding color to an inner surface of said at least one coat.

44. The method of claim 43 further comprising:
   inserting an armature inside said prosthetic skin; and
   filling said prosthetic skin with a fill material selected from a group consisting of silicone or urethane foam.

45. The method of claim 30 further comprising depositing medical grade material on a portion of said prosthetic skin that contacts said stump.

46. The method of claim 30 wherein said synthesizing comprises combining said first and second data sets according to a mapping process.

* * * * *